United States Patent [19]

Joyce et al.

[11] Patent Number: 4,863,867
[45] Date of Patent: Sep. 5, 1989

[54] GAS PERMEABLE BIO-TEST PACK

[75] Inventors: James J. Joyce, Canoga Park; Armineh Khachatoorian, Glendale, both of Calif.

[73] Assignee: Becton, Dickinson and Company, Franklin Lakes, N.J.

[21] Appl. No.: 195,202

[22] Filed: May 18, 1988

[51] Int. Cl.⁴ .............................................. C12M 1/34
[52] U.S. Cl. .................................. 435/287; 435/810; 435/31
[58] Field of Search ..................... 435/287, 31, 810; 422/58, 26, 57, 119; 73/356

[56] References Cited

U.S. PATENT DOCUMENTS 4,486,387 12/1984 Augurt ................................ 422/58
4,636,472 1/1987 Bruso ................................ 435/287

Primary Examiner—Larry Jones
Attorney, Agent, or Firm—Nydegger & Harshman

[57] ABSTRACT

A disposable sterilization bio-test pack for determining the efficacy of sterilizing equipment comprises a porous base pad having a cavity for receiving the sterilization indicator. Porous pads are disposed on opposite sides of the base pad to retain the sterilization indicator within the cavity. The porous medium creates a restriction to the steam's access to the sterilization indicator in order to establish the efficacy of the sterilization equipment.

10 Claims, 2 Drawing Sheets

GAS PERMEABLE BIO-TEST PACK

BACKGROUND OF THE INVENTION

This invention relates generally to packs for testing the efficacy of a sterilization system. More specifically, the invention relates to a disposable test pack which can be used with either a biological indicator or a chemical indicator to determine the efficacy of the sterilization system. The present invention is particularly, though not exclusively, useful for testing the sterilizing equipment used for the sterilization of hospital and medical equipment.

DISCUSSION OF THE PRIOR ART

The sterlization of medical equipment by exposure to steam is typically accomplished by using an autoclave. With this procedure, the equipment to be sterilized is placed within the autoclave and a vacuum is drawn. The sterilization medium, steam, is then introduced into the autoclave to permeate the equipment and sterilize it.

According to standard hospital procedures, steam sterilization equipment needs to be periodically tested to insure the sterilization process is efficacious. Such a test necessarily requires subjecting spores of living microorganisms to the sterilization cycle and subsequently observing whether they have remained viable. To insure that the sterilization process is efficacious by sufficiently challenging the sterilization equipment, these spores need to be protected as well or better than they would ordinarily be protected if lodged in the most inaccessible recesses of the hospital equipment to be sterilized.

Several procedures have been proposed to test the efficacy of steam sterilization equipment. Typical of these, and perhaps the best known and most widely used, is the procedure published by the Association for the Advancement of Medical Instrumentation (A.A.M.I.). According to the A.A.M.I. recommended practice, freshly laundered all-cotton towels are folded by hospital personnel in stacks to construct a test pack into which a biological indicator is embedded. This pack is then subjected to the sterilization cycle.

Although apparently efficacious for its intended purpose, the construction of a test pack according to the A.A.M.I. procedure is labor intensive and the resulting pack is relatively bulky. In light of these limitations, the present invention satisfies the need for a pre-assembled, composite sterilization test pack which is convenient to handle and which will sufficiently challenge steam sterilization equipment. This is accomplished by surrounding a biological indicator with material which will delay steam entry to the indicator and provide the indicator with a degree of thermal insulation.

Prior inventions which have attempted to provide an effective test pack have several shortcomings. First, not all presently available test packs are suitable for use as a biological test pack. For example, consider U.S. Pat. No. 4,486,387 to Augurt for an invention entitled "Disposable Prevacuum Steam Sterilizer Test Device" and U.S. Pat. No. 4,576,795 to Bruso for an invention entitled "Disposable Sterlizer Vacuum Test Pack." While these references provide packs for a chemical test sheet, they do not provide packs with a sized cavity designed to hold and protect a biological test capsule. The present invention provides for a cavity which can hold both a biological and a chemical indicator. Further, the size of this cavity may be varied depending on the desired use.

Test packs with cavities for biological indicators have been proposed, but they still have distinguishable structural differences from the present invention. For example, the invention disclosed in U.S. Pat. No. 4,636,472 to Bruso provides for a biological indicator. However this device, unlike the present invention, has a gas impermeable sheet attached to the porous material. The present invention recognizes that such a gas impermeable layer may not be necessary. Also, the present invention recognizes that the absence of the the gas impermeable sheet simplifies manufacturing, while still providing a test pack that resists steam penetration heating effects on the indicator.

Accordingly, it is an object of the present invention to provide a pre-assembled sterilization test pack which tests the efficacy of steam sterilization equipment by challenging the accessibility of sterilizing steam to the indicator and providing a requisite level of thermal insulation for the indicator. It is yet another object of the present invention to provide a test pack which can easily be altered to change sterilization indicators according to the needs and desires of the operator. Still another object of the present invention is to provide a biological test pack which is small, compact and easily handled by hospital personnel. Another object of the present invention is to provide a test pack which is convenient to use, standardized, cost effective and easily manufactured.

SUMMARY OF THE INVENTION

A preferred embodiment of the novel disposable sterlization test pack includes a base pad comprising a gas permeable porous material having a hole cut therethrough to form a cavity for receiving a sterlization indicator therein. A top pad and a bottom pad of gas permeable porous material are respectively placed against the top and bottom surfaces of the base pad to confine the indicator within the cavity and inhibit the flow of gas to and from the cavity. In an alternative embodiment, the base pad consists of a plurality of stacked sheets. Each sheet is formed with a hole and the holes are aligned to form the cavity. Also, the top pad and the bottom pad may consist of a plurality of stacked sheets.

When subjected to a sterilization cycle, the sterilization indicator positioned in the cavity of the test pack's base pad will react according to the efficacy of the sterilization cycle. As envisioned by the present invention, a biological indicator or a chemical indicator can be used in the test pack. The entire pack, including the base pad and the biological indicator which is held in the cavity by the top and bottom pads, can be covered with a CSR (central supply room) overwrap material and held together with a tape having an indicator ink imprinted thereon to show when a test pack has been subjected to a sterilization process.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

Figure 1:
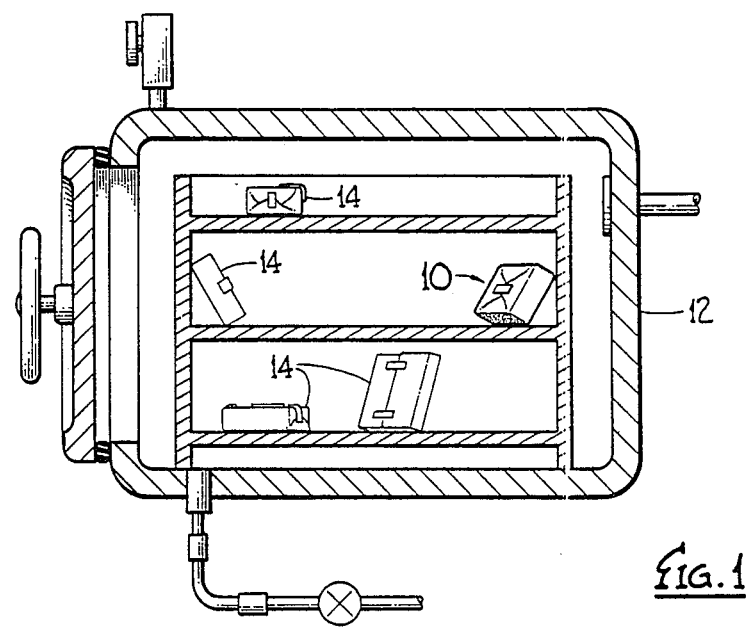
FIG. 1 is a side cross-sectional view of sterilization equipment showing the test pack of the present invention located therein.

FIG. 1 shows bio-test pack 10 of the present invention as it would be placed inside the sterilization equipment 12 for testing the efficacy of the equipment 12. Also shown, placed in equipment 12, are various bundles 14 of medical equipment which require sterilization.

Figure 2:
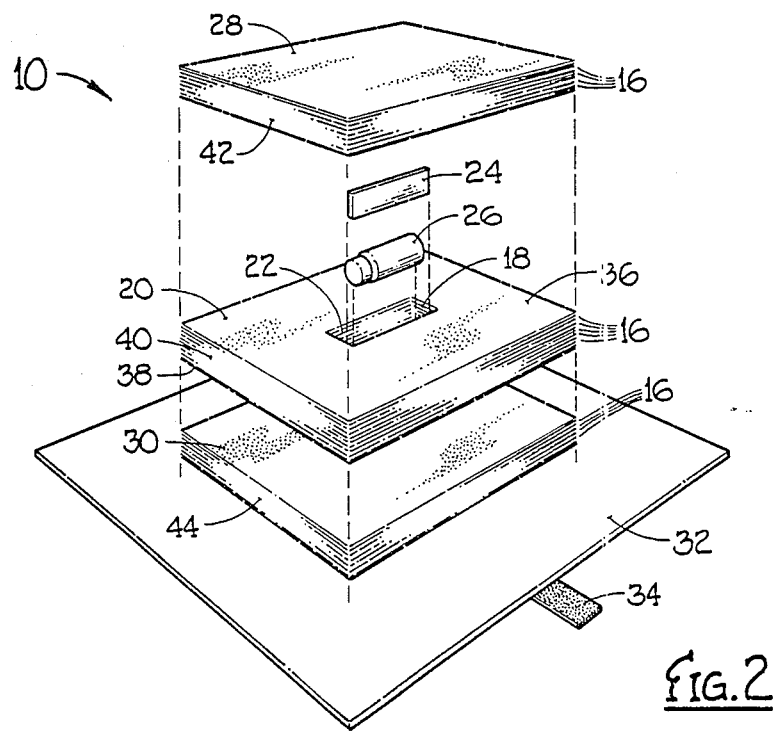
FIG. 2 is an exploded perspective view of the present invention.
Figures 3A, 3B, 3C:
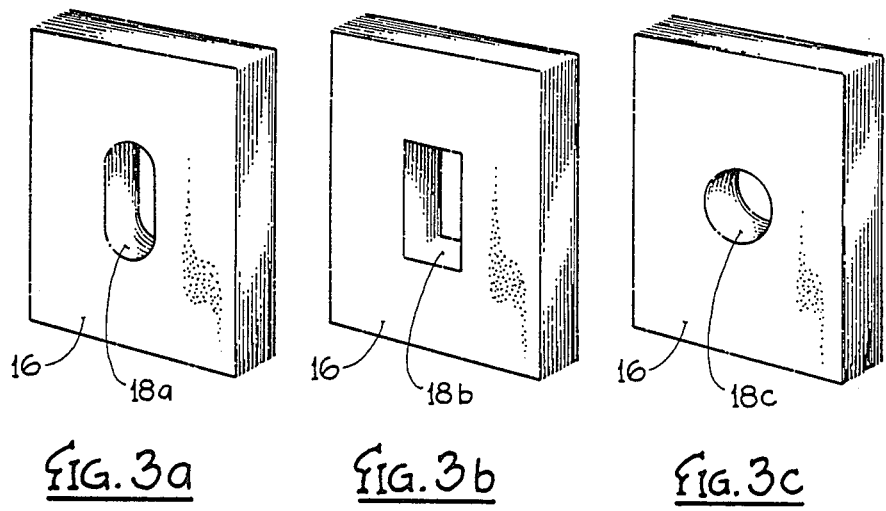
FIG. 3a, 3b and 3c are perspective views of stacked porous sheets used in the present invention showing various holes cut therethrough that can form cavity configurations in which sterilization indicators can be placed.

Referring now to FIG. 2, it can be seen that bio-test pack 10 comprises a base pad 20, a top pad 28 and a bottom pad 30 generally oriented with respect to each other as shown. With specific regard to base pad 20 and reference to FIG. 2, it will be appreciated that base pad 20 may consist of a continuous porous pad or be constructed by stacking together several gas permeable porous sheets 16. As shown in Figures 3a, 3b and 3c, base pad 20 can be formed with holes 18 having several configurations. The variety of holes 18a, 18b and 18c shown respectively in FIGS. 3a, 3b and 3c are only exemplary. Several sheets 16, each having similar hole 18 configurations, are stacked together to form a base pad 20 with a cavity 22. It will be appreciated by the skilled artisan that, depending on the hole 18 configuration, cavity 22 can be formed in various shapes depending upon the needs and desires of the operator and according to the size, shape and configuration of the particular biological test indicator being used. In the preferred embodiment, the sheet 16 comprises a nonwoven gas permeable porous material such as heavy weight index paper which is well known in the pertinent art.

As seen in FIG. 2, base pad 20 is generally box-shaped and has a top surface 36, a bottom surface 38 and an edge 40 defined therebetween. As was the case with cavity 22, the particular shape of base pad 20 can be modified depending on the desires of the operator. However, as will be more clearly appreciated in subsequent discussion, the top surface 36 and the bottom surface 38 are preferably flat in order to engage with top pad 28 and bottom pad 30 in a manner to be subsequently discussed.

Still referring to FIG. 2, it is seen that the cavity 22 is configured with hole 18 to receive a chemical indicator 24 and a biological indicator 26. Any biological indicator of the type well known in the pertinent art is suitable for use with the bio-test pack 10 of the present invention. Further, a chemical indicator 24 of the type described and claimed in U.S. Pat. No. 2,118,144 is appropriate for use in the present invention. In addition to base pad 20, bio-test pack 10 also includes a top pad 28 which preferably comprises a plurality of porous sheets which are stacked to form the box-shaped top pad 28. Unlike base pad 20, top pad 28 is continuous and is not formed with a cavity. In the construction of the bio-test pack 10, top pad 28 is positioned against top surface 36 of base pad 20 with its edge 42 substantially flush with edge 40 of base pad 20. Also, top pad 28 is positioned against base pad 20 in such a way that the biological indicator 26 and the chemical indicator 24 can be held within the cavity 22. Further to this purpose, as also shown in FIG. 2, a bottom pad 30, which preferably comprises a plurality of porous sheets which are stacked to form the box-shaped pad 30 having an edge 44, is disposed against the bottom surface 38 of the base pad 20 with its edge 44 substantially flush with edge 40 of base pad 20. Like the sheets 16 of top pad 28, the sheets 16 of bottom pad 30 are continuous and do not form a cavity. For the purpose of description, the box-shapes described herein are essentially of right parallelepipeds.

In accordance with the above description and the preferred embodiment of the present invention, bottom pad 30 comprises approximately twenty-five undie cut sheets 16; base pad 20 comprises approximately forty die cut sheets 16; and top pad 28 comprises approximately twenty-five undie cut sheets 16. Accordingly, bio-test pack 10 when stacked together will comprise from top to bottom: the gas permeable top pad 28 comprising approximately twenty-five undie cut sheets 16; a gas permeable base pad 20 comprising approximately forty die cut sheets 16 forming a cavity 22 and a gas permeable bottom pad 30 comprising approximately twenty-five undie cut sheets 16.

Figure 4:
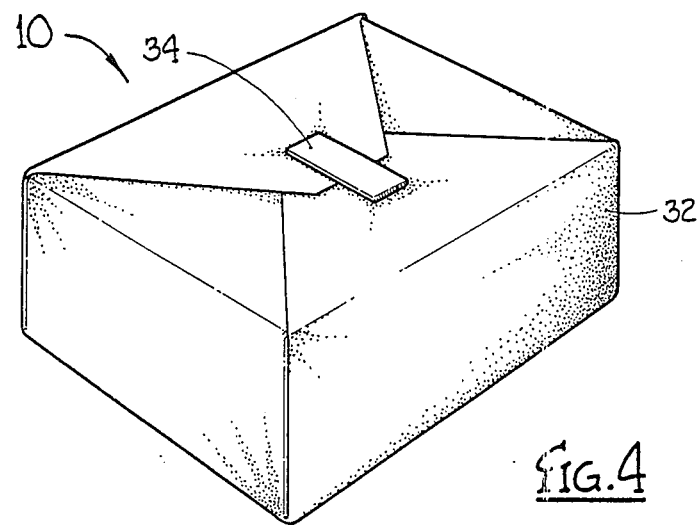
FIG. 4 is a perspective view of the sterilization test pack folded and ready for use in sterilization equipment.

The integrity of the entire bio-test pack 10 can be maintained by folding a disposable CSR wrap 32 around the biotest pack 10 and holding the CSR wrap 32 in place with an autoclave tape 34. As best seen in FIG. 4, bio-test pack 10, when constructed in the above described manner, comprises a self-contained unit which can be easily handled by personnel desiring to test the efficacy of sterilization equipment.

OPERATION

In the operation of the bio-test pack 10 of the present invention, a biological indicator 26 and/or a chemical indicator 24 is placed within the cavity 22 that is formed within the porous base pad 20. A porous top pad 28 is positioned against the top surface 36 of base pad 20 and a porous bottom pad 30 is positioned against the bottom surface 38 of the base pad 20 to confine the chemical indicator 24 or the biological indicator 26 within the cavity 22. The bio-test pack 10 is then wrapped in a disposable CSR wrap 32 and held together by autoclave tape 34 in a manner which allows placement of the bio-test pack 10 into sterilization equipment 12 for testing of the equipment 12. After completion of the sterilization cycle, bio-test pack 10 is removed from equipment 12 and the indicators 24 and 26 are examined to determine the efficacy of the cycle.

The skilled artisan will recognize that the present invention is capable of several variations and modifications. For instance, instead of twenty-five die cut sheets 16 for the top pad 28 as disclosed for the preferred embodiment, top pad 28 may consist of a single porous pad. Thus, an increase in the number of sheets 16 for top pad 28, or an increase in the thickness of pad 28 if it is of unitary construction, will decrease the exposure to indicator 26 to radiant heat. Likewise, the number of sheets 16 used for base pad 20 and bottom pad 30, or their thickness, can be varied according to the desires of the operator. Further, although the preferred dimensions of sheets 16 are 4.5 inches × 6 inches when used, these dimensions can also be changed to vary the resistance of bio-test pack 10 to meet the particular needs and desires of the operator.

While the particular test pack as herein shown and disclosed in detail is fully capable of obtaining the objects and providing the advantages herein before stated, it is to be understood that it is merely illustrative of the presently preferred embodiment of the invention and that no limitations are intended to the details of construction or design herein shown other than as defined in the appended claims.

I claim:

1. A disposable bio-test pack for testing the efficacy of a sterilization process essentially consisting of:
   a sterilization indicator;
   a porous base pad with a hole formed therethrough to establish a cavity for receiving said sterilization indicator therein, said base pad having a top surface, a bottom surface and an edge therebetween;
   a porous top pad disposed against said top surface to cover said cavity; and
   a porous bottom pad disposed against said bottom surface to hold said sterilization indicator in said cavity.

2. A disposable bio-test pack as cited in claim 1 further consisting of a gas permeable porous overwrap surrounding said pack to maintain the integrity thereof.

3. A disposable bio-test pack as cited in claim 2 wherein said sterilization indicator is a biological indicator.

4. A disposable bio-test pack as cited in claim 2 wherein said sterilization indicator is a chemical indicator.

5. A disposable bio-test pack as cited in claim 2 wherein said base pad is a plurality of gas permeable porous sheets, said top pad is a plurality of gas permeable porous sheets and said bottom pad is a plurality of said gas permeable porous sheets.

6. A disposable test pack for a biological indicator essentially consisting of:
   a porous base pad having a top surface and a bottom surface and an edge therebetween, said base pad formed with a cavity therethrough surrounded by said edge; and
   a porous top pad and a porous bottom pad respectively positioned against said top and bottom surfaces to hold said biological indicator in said cavity.

7. A disposable test pack as cited in claim 6 wherein said base pad consists of a plurality of sheets having holes therethrough, said sheets being stacked to align said holes to form said cavity.

8. A disposable test pack as cited in claim 7 wherein said top pad and said base pad are a plurality of stacked sheets.

9. A disposable test pack as cited in claim 8 further consists of a gas permeable porous overwrap surrounding said pack to maintain the integrity thereof.

10. A method for determining the efficacy of steam sterilization cycle of an autoclave essentially consisting of the steps of:
    (A) Placing in said autoclave a test pack with a biological indicator, said test pack comprising a porous base pad having a top surface and a bottom surface and an edge therebetween, said base pad formed with a cavity surrounded by said edge, and a porous top pad and a porous bottom pad respectively positioned against said top and bottom surfaces to hold said biological indicator in said cavity;
    (B) Cycling said autoclave;
    (C) Removing said test pack from said autoclave to retrieve said biological indicator; and
    (D) Testing said biological indicator for the presence of viable biological spores.

* * * * *